(12) United States Patent
Tekulve et al.

(10) Patent No.: US 7,921,874 B2
(45) Date of Patent: Apr. 12, 2011

(54) FLOW VARIATION VALVE ASSEMBLY

(75) Inventors: Kurt J. Tekulve, Elletsville, IN (US); Ram H. Paul, Jr., Bloomington, IN (US); Julie E. Urbanski, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1032 days.

(21) Appl. No.: 11/272,237

(22) Filed: Nov. 10, 2005

(65) Prior Publication Data

US 2006/0118189 A1 Jun. 8, 2006

Related U.S. Application Data

(60) Provisional application No. 60/627,243, filed on Nov. 12, 2004.

(51) Int. Cl.
*F16K 15/14* (2006.01)
(52) U.S. Cl. ..................... 137/513.3; 137/846
(58) Field of Classification Search ............... 136/846; 623/2.12, 212, 1.24; 137/846, 493–493.9, 137/513.3, 512.4; 604/9, 99.02, 915, 247
See application file for complete search history.

(56) References Cited

U.S. PATENT DOCUMENTS

| | | |
|---|---|---|
| 335,719 A | 2/1886 | Rein |
| 511,728 A | 12/1893 | Deming |
| 545,769 A | 9/1895 | Bowman |
| 2,082,972 A * | 6/1937 | Perry ............................ 137/232 |
| 3,308,798 A * | 3/1967 | Snider ............................ 123/572 |
| 3,325,143 A | 6/1967 | Phillips |
| 3,356,093 A * | 12/1967 | Monahon ..................... 604/99.02 |
| 3,612,102 A | 10/1971 | Hulsey |
| 3,860,007 A * | 1/1975 | Binard et al. ............... 604/99.02 |
| 4,181,145 A * | 1/1980 | Mitchell ..................... 137/493.8 |
| 4,259,951 A * | 4/1981 | Chernack et al. ......... 128/200.14 |
| 4,501,374 A * | 2/1985 | Robertson ..................... 220/86.2 |
| 4,535,818 A | 8/1985 | Duncan et al. |
| 4,535,819 A | 8/1985 | Atkinson et al. |
| 4,645,496 A | 2/1987 | Oscarsson |
| 4,654,027 A | 3/1987 | Dragan et al. |
| 4,802,506 A | 2/1989 | Aslanian |
| 4,819,637 A * | 4/1989 | Dormandy et al. ........... 606/195 |
| 5,085,636 A * | 2/1992 | Burns ......................... 604/99.04 |
| 5,108,416 A | 4/1992 | Ryan et al. |
| 5,112,301 A * | 5/1992 | Fenton et al. ................... 604/30 |
| 5,156,600 A * | 10/1992 | Young ........................... 604/247 |
| 5,224,938 A * | 7/1993 | Fenton, Jr. .................... 604/247 |
| 5,304,155 A | 4/1994 | Lui |
| 5,329,921 A | 7/1994 | Socaris et al. |
| 5,817,068 A | 10/1998 | Urrutia |
| 5,924,452 A | 7/1999 | Szpara et al. |
| 6,024,729 A | 2/2000 | Dehdashtian et al. |
| 6,044,859 A | 4/2000 | Davis |
| 6,092,551 A | 7/2000 | Bennett |
| 6,176,843 B1 | 1/2001 | DiCaprio et al. |

(Continued)

*Primary Examiner* — John Rivell
*Assistant Examiner* — Macade Brown
(74) *Attorney, Agent, or Firm* — Brinks Hofer Gilson & Lione

(57) ABSTRACT

A non-implantable valve assembly and a method for controlling flow rates in a medical device are provided. The valve assembly includes a valve member being dimensioned for reception at least partially within a lumen of the medical device. The valve member includes a flow regulator for controlling flow rates in a first direction having a first rate and a second direction having a second rate. The second rate is greater than the first rate.

16 Claims, 10 Drawing Sheets

U.S. PATENT DOCUMENTS

| | | |
|---|---|---|
| 6,416,499 B2 | 7/2002 | Paul, Jr. |
| 6,419,657 B1 | 7/2002 | Pacetti |
| 6,428,520 B1 | 8/2002 | Lopez et al. |
| 6,562,069 B2 * | 5/2003 | Cai et al. ............... 623/2.12 |
| 7,360,556 B2 * | 4/2008 | Mijers ............... 137/493.9 |
| 7,717,116 B2 * | 5/2010 | Mijers ............... 128/207.15 |
| 2003/0085373 A1 | 5/2003 | Dehdashtian |
| 2003/0144670 A1 | 7/2003 | Pavcnik et al. |
| 2004/0010265 A1 | 1/2004 | Karpiel |
| 2004/0059296 A1 | 3/2004 | Godfrey |

* cited by examiner

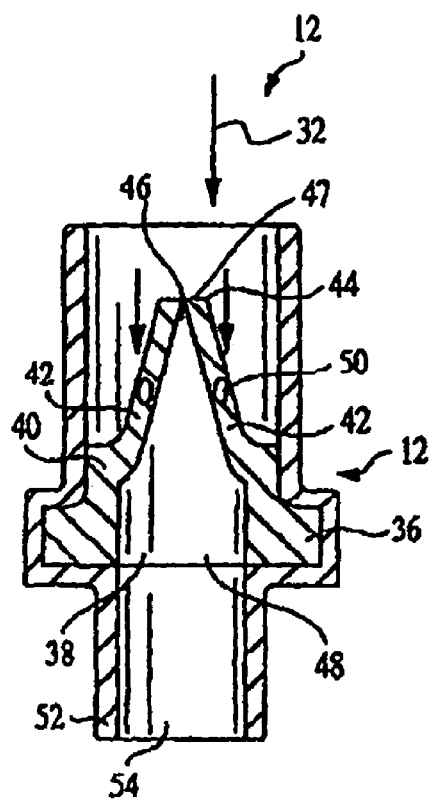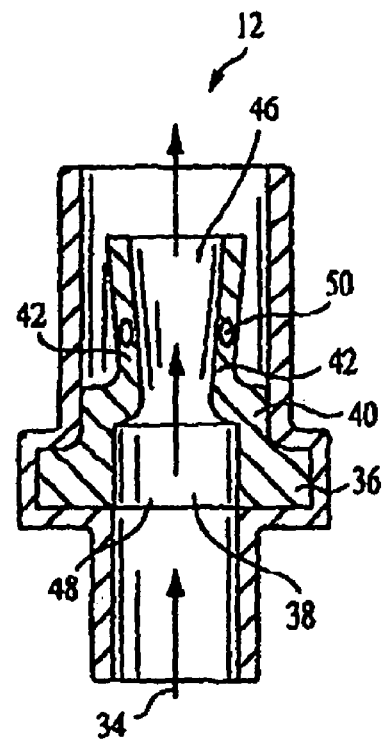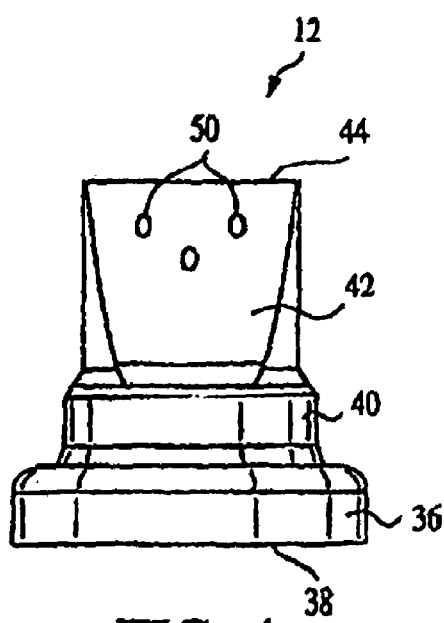

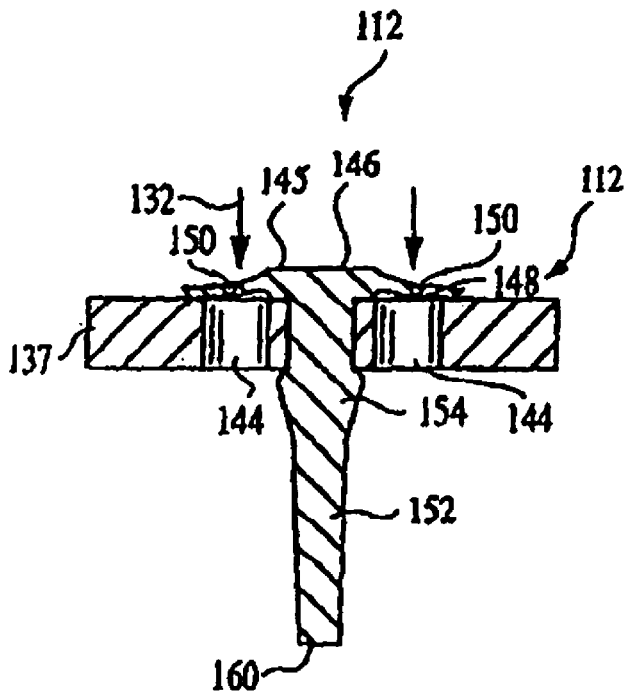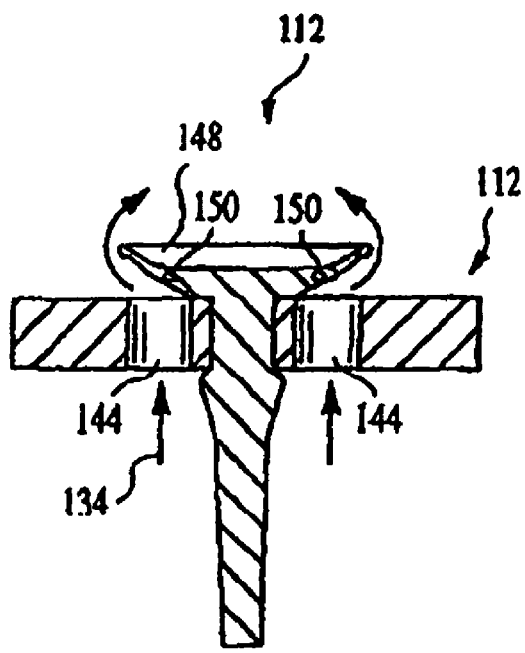
FIG. 5    FIG. 6
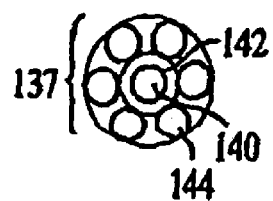
FIG. 7

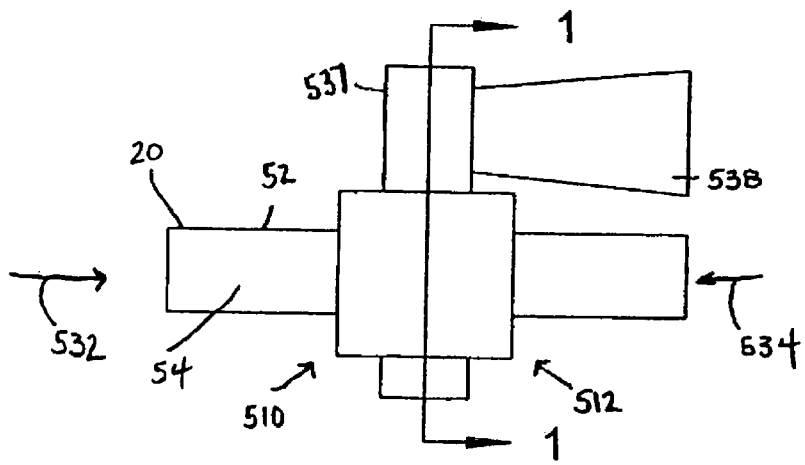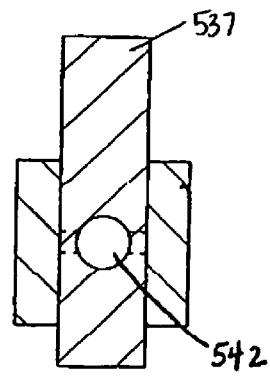
FIG. 13  FIG. 14
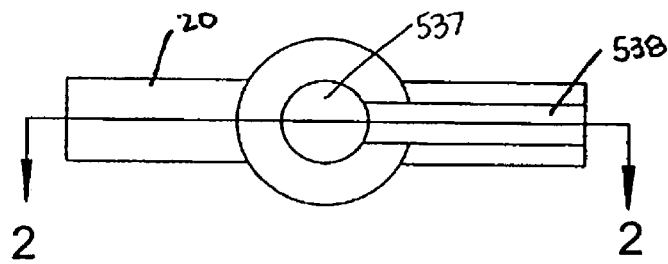
FIG. 15
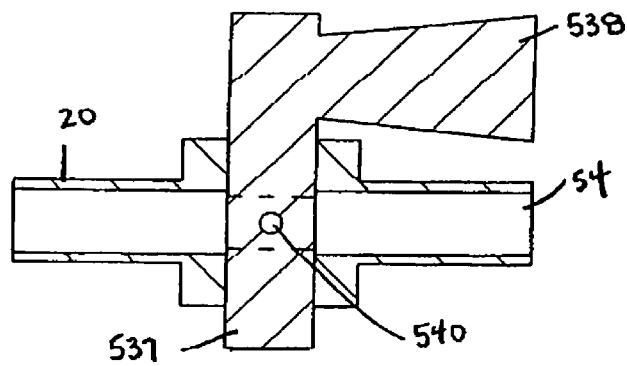
FIG. 16

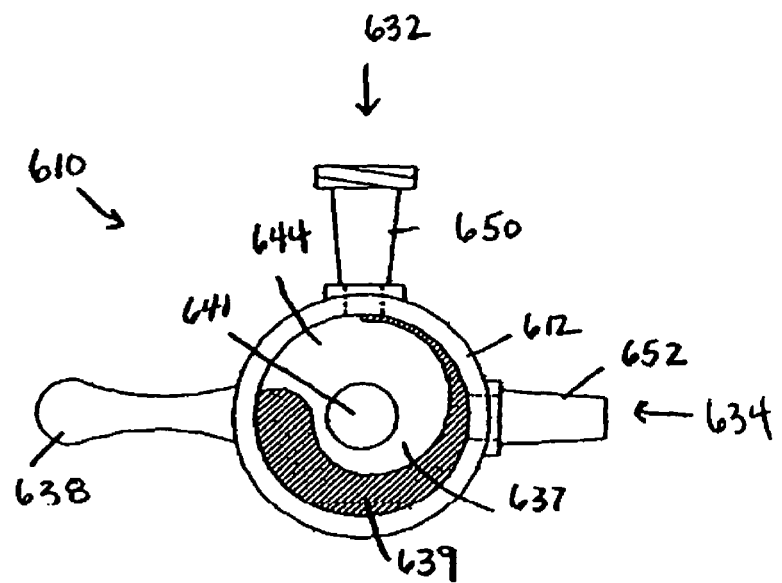
FIG. 18
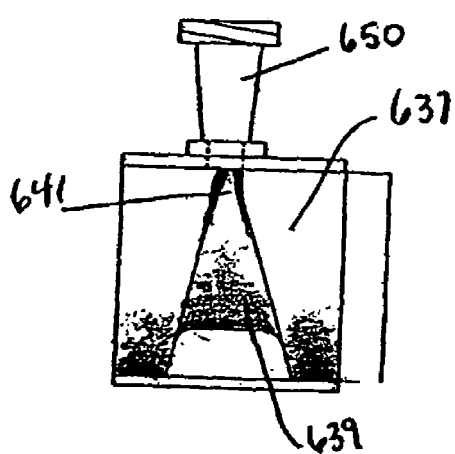 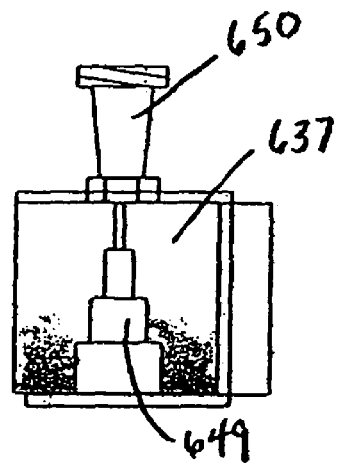
FIG. 19A     FIG. 19B

FLOW VARIATION VALVE ASSEMBLY

This application claims the benefit of U.S. Provisional Application No. 60/627,243, filed Nov. 12, 2004, the entirety of which is incorporated by reference herein.

TECHNICAL FIELD

This invention relates generally to medical devices, and more particularly to medical devices for controlling the flow rates through catheter introducers and other sheaths, cannulae, catheters, trocars, scopes and the like.

BACKGROUND OF THE INVENTION

It is now well known to perform a variety of surgical procedures by the introduction of an interventional device into the body, for example, into an arterial or venous blood vessel, or into a laparoscopic or other cavity artificially maintained in the body. Typical of the former type of procedure are coronary angiography (e.g., where an X-ray contrast fluid is inserted into the coronary artery) and percutaneous transluminal coronary angioplasty (PTCA). These and other procedures involve the introduction of an interventional device, such as a catheter (open or closed end), a wire guide, a balloon, a stent, an atherectomy device, or the like into the vessel or cavity in question. The devices may be non-implantable and removed following the procedure or shortly thereafter. Alternatively, the devices may be implantable, remaining in the vessel of the patient post implantation.

Procedures for introducing a catheter into a blood vessel include the cut-down method and the Seldinger technique. The Seldinger technique is well known, and first involves opening a blood vessel with a needle, inserting a guide wire into the vessel through the lumen of the needle, withdrawing the needle and inserting a dilator over the guide wire. The dilator is located inside an associated sheath which is also inserted into the vessel, and the dilator is sealed to the sheath by a hemostasis or hemostatic valve through which the dilator passes. The dilator is removed, and the catheter inserted through the sheath and into the vessel.

The catheter may include a balloon on the distal portion thereof. The tip of the catheter is advanced to the site of treatment, for example, an atherosclerotic plaque, the balloon being deflated during the insertion. Once in position across the treatment site, the flexible, expandable, preformed balloon is inflated. The inflated balloon may be used, for example, to relieve stenosis at the atherosclerotic plaque, at least partially. Typically, the balloon is inflated by supplying a pressurized fluid through an inflation lumen in the catheter. The balloon catheter may also be used for delivering a medical device such as an intravascular stent to a treatment site. After completion of the procedure, the balloon is deflated to a small profile so that the catheter may be withdrawn from the patient's vasculature and blood flow resumed through the dilated vessel.

Currently, inflation and deflation of the balloon occur at the same rate. Rapid inflation of the balloon may damage vessels or provide less precision in the placement of an implantable medical device, such as an intravascular stent. Rapid deflation of the balloon is desirable to prevent prolonged occlusion of blood flow in the vessel. Valves for use with medical devices have previously been used for flow control by preventing flow in a first direction and allowing flow in a second direction. Therefore, it is highly desirable to provide a non-implantable valve assembly that allows different flow rates in medical devices, such as for inflation and deflation of the balloon on the catheter at the site of treatment. The non-implantable valve assembly of the present invention will allow variation in flow, providing a slower flow rate in a first direction and a more rapid flow rate in a second direction.

BRIEF SUMMARY

The foregoing problems are solved and a technical advance is achieved in an illustrative valve assembly that provides a slow inflation rate and a rapid deflation rate.

In one aspect of the present invention, a non-implantable valve assembly for controlling flow rates in a medical device is provided. The valve assembly includes a valve member being sized and shaped for reception at least partially within a wall defining a lumen of the medical device. The valve member includes a flow regulator for controlling flow rates in a first direction having a first rate and a second direction having a second rate. The second rate is greater than the first rate.

In another aspect of the present invention, a method of controlling flow in a medical device in a first direction and a second direction is provided. The method includes providing a non-implantable valve assembly and positioning the valve assembly in a wall defining a lumen of the medical device. The valve assembly includes a valve member being sized and shaped for reception at least partially within a wall defining a lumen of the medical device and the valve member includes a flow regulator for controlling flow rates in the first direction having a first rate and the second direction having a second rate. The second rate is greater than the first rate.

In another aspect of the present invention, a non-implantable flow control assembly for controlling flow rates in a medical device is provided. The flow control assembly includes a multipositional member sized and shaped for reception within a wall defining a lumen of the medical device and a control member operably connected to the multipositional member for selecting the first flow rate or the second flow rate. The multipositional member at least one first opening defined therein for controlling the first flow rate and at least one second opening defined therein for controlling the second flow rate. The second flow rate is greater than the first flow rate.

BRIEF DESCRIPTION OF THE DRAWINGS

FIG. 2 is a sectional view of an embodiment of the valve assembly of the present invention showing flow in a first direction; and FIG. 3 is a sectional view of the embodiment shown in FIG. 2 showing flow in a second direction;

FIG. 4 is a side elevational view of the embodiment shown in FIG. 2:

FIG. 5 is a sectional view of another embodiment showing flow in a first direction; and FIG. 6 is a sectional view of the embodiment shown in FIG. 5 showing flow in a second direction;

FIG. 7 is a top elevational view of the annular member of the embodiment shown in FIG. 5;

FIG. 13 is a side view of an alternative embodiment of the present invention;

FIG. 14 is a sectional view through the line 1-1 shown in FIG. 13;

FIG. 15 is a top view of the embodiment shown in FIG. 13;

FIG. 16 is a sectional view through the line 2-2 shown in FIG. 15;

FIG. 18 is a side, sectional view of an alternative embodiment of the present invention;

FIG. 19A is a front sectional view of the embodiment shown in FIG. 18;

FIG. 19B is a front sectional view of an alternative groove pattern for the embodiment shown in FIG. 18;

DETAILED DESCRIPTION OF THE DRAWINGS AND THE PRESENTLY PREFERRED EMBODIMENTS

Figure 1:
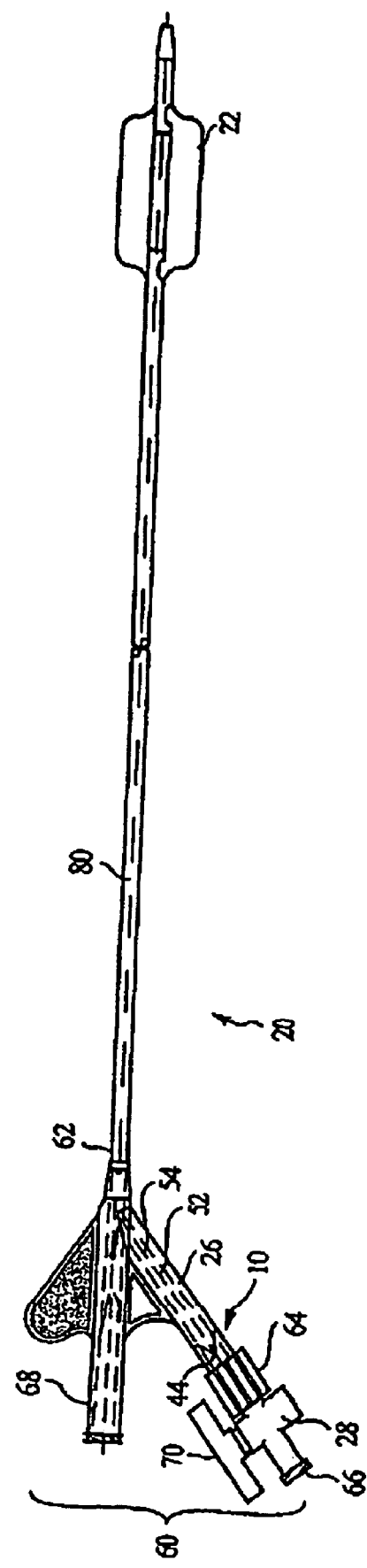
FIG. 1 is a side view of an embodiment of the valve assembly of the present invention shown with a medical device.

FIG. 1 illustrates an embodiment of the present invention. A valve assembly 10 useful as a flow variation valve in a fluid flow path of a medical device is shown. More particularly, the valve assembly 10 is shown as incorporated into a catheter 20 and as such finds particular utility as a flow variation valve for regulation of the inflation and deflation of a balloon 22 of the catheter 20. The valve assembly 10 may be incorporated into the catheter 20 in a flow path 26 downstream from a stopcock 28. Alternatively, the valve assembly 10 may be incorporated into the stopcock 28 as described in more detail below.

As shown in FIGS. 2-4, one embodiment of the valve assembly 10 is a "duck bill" type valve assembly 12 that allows flow to occur in a first direction 32 (FIG. 2) and a second direction 34 (FIG. 3). The valve assembly 12 includes an annular flange 36 at a first end 38 of the valve assembly 12 and an annular shoulder 40 connected to the flange 36. A pair of flow regulator leaflets 42 extends from the shoulder 40, each leaflet 42 having a generally planar configuration. The leaflets 42 converge at a second end 44 of the valve assembly 12, and the leaflets 42 meet along a line 46 to form a closed slit 47. Three or more leaflets 42 may also be used (not shown) wherein the leaflets 42 meet to form a closed line or point at the second end 44. The flange 36 defines a flange opening 48 formed in the first end 38 of the valve assembly 12.

As shown in FIGS. 2-4, the leaflets 42 include leaflet openings 50 defined therein. One of skill in the art will recognize that at least one opening 50 is defined in at least one of the pair of leaflets 42. More preferably, a plurality of openings 50 may be defined in the pair of leaflets 42. The number and size and shape of the openings 50 will depend on the desired inflation rate, the overall catheter construction and can be readily determined by one of skill in the art. By way of example, but not limited to the following, the openings 50 may be circular, partially circular, square, triangular, ovoid, and teardrop shaped.

The flange 36 and the annular shoulder 40 are dimensioned such that the flange 36 may be received within a wall 52 defining a lumen 54 of the catheter 20. Preferably, the flange 36 and the shoulder 40 are cylindrical to fit with the cylindrical wall 52 of the catheter 20. However, any shape may be used for the flange 36 and the shoulder 40 as long as the flange 36 fits within the wall 52. The flow path is directed through the openings 50 in the leaflets 42 in the first direction 32 and through the opening 48 in the flange 36 in the second direction 34.

The orientation of the valve assembly 10 in the lumen 52 of the catheter 20 is shown in FIG. 1. In an embodiment of the present invention, the catheter 20 may include a Y-shaped fitting 60 at a first end 62 of the catheter 20 which includes a balloon inlet lumen 64 having an opening 66 and the stopcock 28. The fitting 60 may further include a distal inlet 68. The valve assembly 10 is located in the balloon inlet lumen 64 and the first end 44 of the valve assembly 10 is oriented toward the opening 66 in the balloon inlet lumen 64. The flow path in the first direction flows from the opening 66 in the inlet 64 to the balloon 22 and the second direction flows from the balloon 22 to the opening 66. When a separate valve assembly 10 is included, the stopcock 28 is positioned between the opening 66 and the valve assembly 10. The stopcock 28 allows flow into and out of the lumen 52 and may have two positions, opened and closed, with respect to flow through the stopcock 28.

The valve assembly 10 of the present invention may be formed from any material known to one of skill in the art, including, but not limited to silicone, fluorosilicone, fluoro elastomer, fluorocarbon and other elastomeric materials. In the preferred embodiment for reception within the catheter 20, the valve assembly 10 may be formed from silicone or fluorosilicone, preferably having a Shore A hardness of about 45-65, more preferably about 50-60. Preferably, the material or materials from which the valve assembly 10 is formed are stable to conditions necessary to sterilize the device.

In operation, the valve assembly 10 allows a slower first rate in the first flow direction 32 and a greater flow rate in the second flow direction 34. The flow rate as described herein refers to the inflation and deflation rates and includes air flow and fluid flow, preferably fluid flow. Flow will be described herein using fluid flow. Fluid may be introduced into the opening 66 in the catheter 20 using a syringe or by any method known to one of skill in the art. The stopcock 28 is in a first, open position 70 wherein the lumen 54 is fully open and fluid flows into the flow path 26. To stop the flow, the stopcock 28 is placed in a second position (not shown) thereby closing the lumen 54. As shown in FIG. 2, fluid flows into the lumen 54 defined by the wall 52 to the valve assembly 10 in the first direction 32 and the leaflets 42 form the closed slit 47 in the first direction which generally prevents the fluid from flowing through the slit 47. One of skill in the art will appreciate that preventing the flow of fluid through the slit 47 need not be absolute and a small amount of flow through the slit 47 in the first direction 32 is within the scope of the present invention. Flow in the first direction 32 flows through the leaflet openings 50 at a first rate. Fluid flows to the balloon 22 and the balloon 22 is inflated at the first rate. In the second direction 34, the fluid flows through the opening 48 and the open leaflets 42 at a second rate. As shown in FIG. 3, when the flow direction 34 flows into the flange opening 48, the leaflets 42 are spaced apart from each other with the fluid flowing therebetween allowing a greater second flow rate in the second direction 34. The balloon 22 is deflated when the fluid flows in the second direction 34 at the second rate.

The second rate is greater than the first rate providing faster deflation to decrease the amount of time the vessel is occluded by the balloon 22. The slower first rate preferably allows for less injury and more precise placement of the balloon 22, or a stent placed on the end of a catheter (not shown) in the vessel than when a single rate is used for inflation and deflation of the balloon 22.

Without wishing to be bound to the particulars described below, an exemplary comparison of the first flow rate and the second flow rate is described herein for use with a large occlusion balloon catheter, similar catheters are available from Cook, Inc., Bloomington, Ind. The exemplary catheter 20 may be a balloon catheter, as shown in FIG. 1, having a length of about 100 to about 120 cm and an exterior diameter of about 4-6 mm. The preferred first rate and second rate are based on inflation of the balloon 22 with 20 cc of fluid injected into the opening 66 of the inlet lumen 64 and subsequent deflation when the fluid is removed from the balloon 22 and flows in the second direction 34. The preferred first flow rate for inflation of the balloon 20 is about 30 to about 45 seconds, more preferably about 35 to about 40 seconds. The preferred second flow rate for deflation of the balloon 22 is about 2 to about 12 seconds, more preferably about 3 to about 8 seconds.

The details and mechanics of balloon inflation and specific overall catheter construction will vary according to the particular design involved in any given instance, and are known to one of skill in the art. Such details are only shown schematically herein. All variations are acceptable for use with this invention. The first flow rate and the second flow rate will vary depending on the dimension of the catheter 20 and the balloon 22, with the second rate preferably being greater than the first rate.

As shown in FIGS. 5-7, another embodiment of the valve assembly 10 is shown as an "umbrella" type valve assembly 112. As discussed above for the valve assembly 12, the valve assembly 112 allows flow to occur in a first direction 132 (FIG. 5) having a first flow rate and a second direction 134 (FIG. 6) having a second flow rate.

The valve assembly 112 includes an annular member 137 that is dimensioned to fit within the wall 52 of the catheter 20 and may be any shape that fits within the wall 52. The member 137 further includes a central opening 140 defined in the central portion 142 of the member 137. At least one additional opening 144, more preferably, a plurality of openings 144, are formed in the member 137 surrounding the central opening 140 as shown in FIG. 7. The number and dimensions of the openings 144 will depend on the desired first and second flow rates, and can be readily determined by one of skill in the art.

The valve assembly 112 further includes an umbrella-shaped flow regulator member 146 that fits together with the central opening 140 of the annular member 137 as shown in FIGS. 5 and 6. An annular flange 148 extends radially at a first end 145 of the member 146. The member 146 further includes a stem 152 at a second end 160 and an annular shoulder 154 extending radially from the stem 152. The member 146 fits in the central opening 140 with the shoulder 154 below the member 137 and the flange 148 above the member 137. The flange 148 extends radially and covers the openings 144 in the member 137. The flange 148 further includes a plurality of openings 150 defined in the flange 148. The openings 150 in the flange 148 are positioned over the openings 144 in the member 137. As described above for the openings 50, the number and dimensions of the openings 150 will depend on the desired first flow rate for inflation, catheter construction, etc. and can be readily determined by one of skill in the art.

The valve assembly 112 is formed from any flexible material known to one of skill in the art, preferably an elastomer. The flange 148 and the member 137 do not need to be formed from the same material. The material for the valve assembly 112 allows the flange 148 to form a flattened shape that fits against the member 137 to cover the openings 144 in the first flow direction 132. The flange 148 may form a convex shape in the second flow direction 134 to allow fluid to flow through openings 144 in the member 137.

The placement of the valve assembly 112 is similar to the placement and operation of the valve assembly 12 describe above with the member 137 positioned in the wall 52 defining the lumen 54 of the catheter 20 and the first end 145 of the member 146 positioned toward the opening 66. A stopcock 28 may be positioned in the inlet lumen 64 positioned between the opening 66 and the valve assembly 112.

In operation, the fluid flows in the first direction 132 from the opening 66 to the balloon 22 at a first rate. In the first direction 132, the flange 148 is flattened against the member 137 and covering the openings 144. The fluid flows primarily through the openings 150 to inflate the balloon 22 at the first rate. In the second direction 134, described above, the flange 148 is lifted by the fluid flow to form a convex disc extending away from the member 137, thereby allowing the fluid to flow through the openings 144 in the member 137 in the second direction 134. The balloon 22 is deflated when the fluid flows in the second direction 134 at the second rate. The first and second flow rates are described above.

Figure 8A:
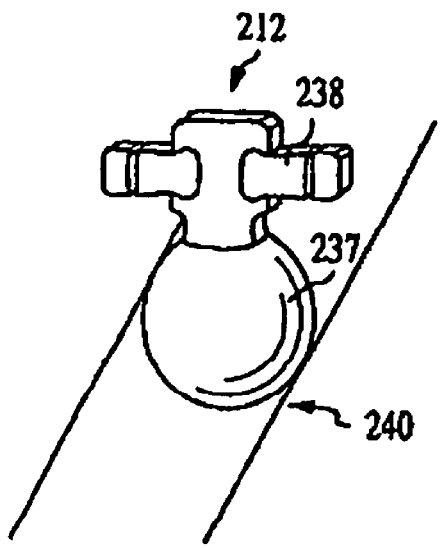
FIG. 8A is a perspective view of the another embodiment showing the flow control assembly in a first position.
Figure 8B:
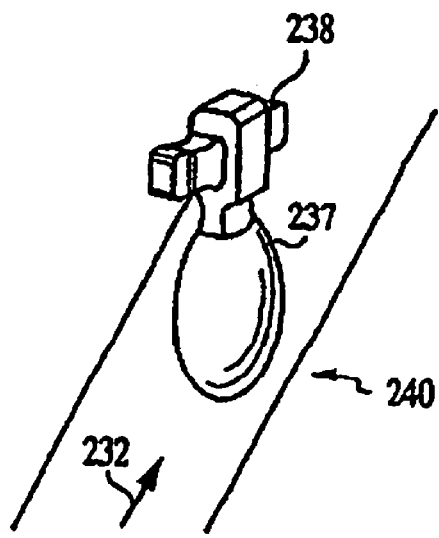
FIG. 8B is a perspective view of the embodiment shown in FIG. 8A showing the flow control assembly in a second position.
Figure 8C:
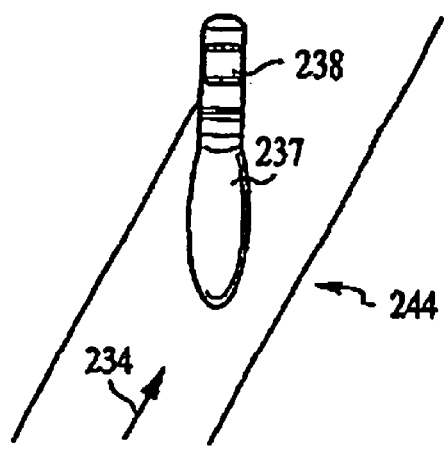
FIG. 8C is a perspective view of the embodiment shown in FIG. 8A showing the flow control assembly in a third position.

As shown in FIGS. 8A-C, another embodiment of the valve assembly 10 is shown as a multipositional stopcock 212. The stopcock 212 may have multiple positions to control the flow in a first direction 232 and a second direction 234 similar to the first and second directions 32, 34 described above. The stopcock 212 includes a moveable member 237 positioned through the wall 52 defining the lumen 54 of the catheter 20 and a handle 238 external to the wall 52 to control the position of the movable member 237. The member 237 may be used to control the flow through the pathway 26 of the catheter 20 by positioning the member 237 in different lumen positions and the member 237 is sized and shaped to fit within the lumen 54 defined by the wall 52 of the catheter 20. By way of example, the multiple positions for the member 237 are shown in FIGS. 8A-8C. FIG. 8A illustrates the member 237 in the closed position 240 wherein flow is prevented in either direction 232 or 234. FIG. 8B illustrates the member 237 in position 242 to allow flow at the first rate wherein the member 237 allows partial flow through the lumen 54, preferably in the first direction 232 as shown in FIG. 8B, although flow may also proceed in the second direction 234. FIG. 8C illustrates the member 237 in position 244 to allow flow at the second rate wherein the member 237 allows flow at a greater rate than the position shown in FIG. 8B. Preferably the flow at the second rate flows in the second direction 234, although flow in the first direction 232 at the second rate is possible. The stopcock 212 may be used together with the stopcock 28.

Figure 9:
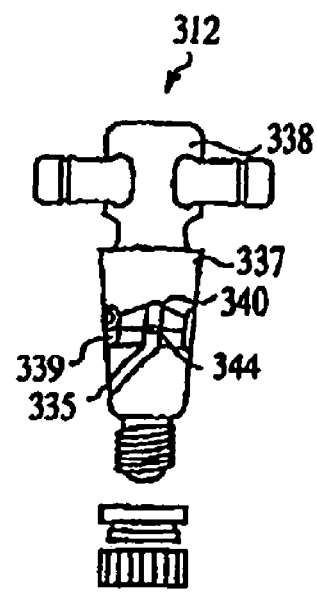
FIG. 9 is a side elevational view of another embodiment of the present invention.
Figure 10A:
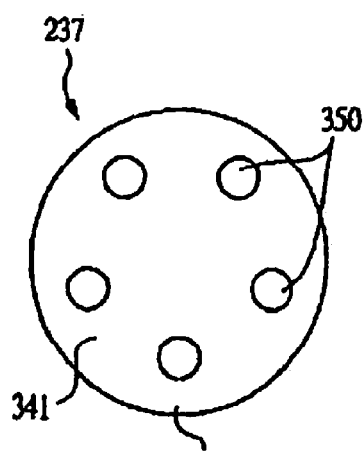
FIG. 10A is a sectional view of a portion of the flow control assembly of the embodiment shown in FIG. 9.
Figure 10B:
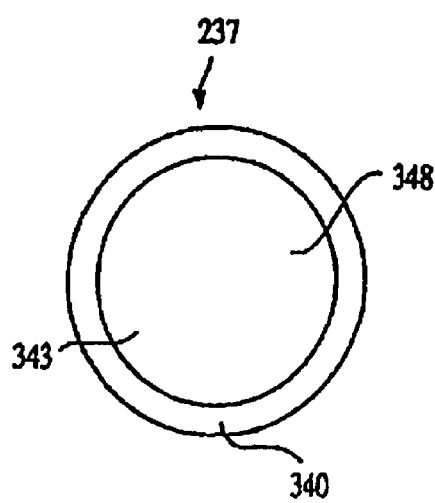
FIG. 10B is a sectional view of a portion of the flow control assembly of the embodiment shown in FIG. 9.
Figure 10C:
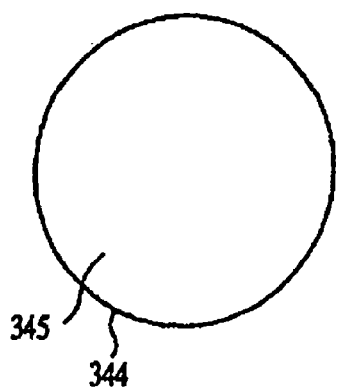
FIG. 10C is a sectional view of a portion of the flow control assembly of the embodiment shown in FIG. 9.

As shown in FIGS. 9-10C, an embodiment of the valve assembly 10 is a multipositional stopcock 312. The stopcock 312 includes a plurality of lumen positions 339, 340, 344 each having a member to fit within the wall 52 defining the lumen 54 when a handle 338 is turned to the position for each member. For example, in a stopcock 312 having three lumen positions, a first position 339 is defined by a first member 341 that may allow flow at the first rate. The first member 341 of the movable member 337 includes at least one opening 350 defined therethrough, preferably a plurality of openings 350, to allow flow through the lumen 54 of the catheter 20 in at the first rate. At a second position 340, defined by a second member 343, an opening 348 is defined therethrough for flow at a second rate. A third position 344, defined by a third member 345, may have no openings and provide an off position for the member 337 whereby flow in the lumen 54 is stopped. The handle 338 external to the catheter 20 moves to control the position of the members 341, 343, and 345 to control the flow through the lumen 54. In operation, flow from the opening 66 enters the multipositional stopcock 312 in a first direction though one of the members 341, 343 and exits the stopcock 312 through a common opening 335 to the flow path 26 to inflate the balloon 22. In the second direction, flow exits the balloon 22 through the flow path 26 to the common opening 335 in the stopcock 312 and out through member 341 or 343 to the opening 66. Preferably, flow in the first direction is through the member 341 at the first rate and flow in the second direction is through the member 343 at the second rate. The first rate and the second rate are as described above. The stopcock 312 may be used together with the stopcock 28.

Figure 11:
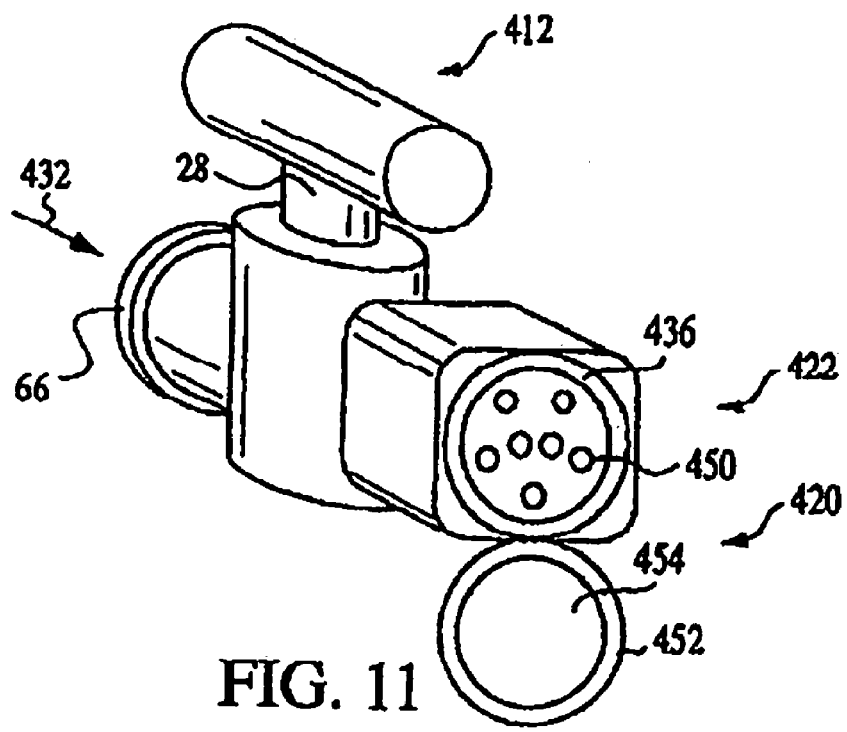
FIG. 11 is a sectional view of an alternative embodiment of the present invention in a first position.
Figure 12:
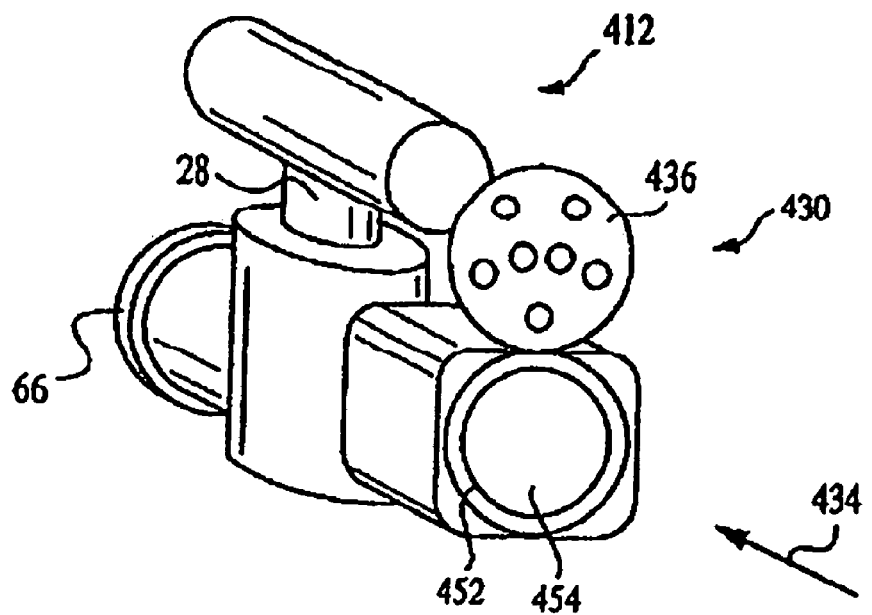
FIG. 12 is a sectional view of the embodiment shown in FIG. 11 in a second position.

In an alternative embodiment of the present invention, the valve assembly 10 may be a "push button" valve assembly 412, as shown in FIG. 11. The valve assembly 412 is adapted to control the flow in the lumen 54 of the catheter 20 as described above for the valve assembly 12. The valve assembly 412 includes a slidable member 420 that is at least partially sized to fit in the wall 52 defining the lumen 54. The slidable member 420 moves between a first position 422 shown in FIG. 11 and a second position 430 shown in FIG. 12. The slidable member 420 includes an annular member 436 that may be slid into the lumen 54 in the first position 422 and be sized and shaped to fit within wall 52 of the lumen 54 to control flow a first rate for inflation of the balloon 22 of the catheter 20. The member 436 includes at least one opening 450 defined in the member 436, preferably a plurality of openings 450, for flow therethrough at the first rate. The direction of flow may be in a first direction 432 or a second direction 434 through the member 436, preferably in the first direction 432. The slidable member 420 may further include a second annular member 452 that may be slidably inserted into the wall 52 defining the lumen 54 in the second position 430 when the member 436 is slid out of the wall 52 from the first position 422. The member 452 is adapted to fit within the wall 52 and includes an opening 454 defined in the member 452 for flow therethrough. Flow may be controlled at the second rate for deflation of the balloon 22 of the catheter 20, preferably in the second direction 434 as shown in FIG. 12. The flow rates are described above.

In another embodiment of the present invention, shown in FIGS. 13-17, a valve assembly 510 is illustrated. The valve assembly 510 includes a multiposition stopcock 512. The stopcock 512 may control the flow in a first direction 532 and a second direction 534 similar to the first and second directions 32, 34 described above. The stopcock 512 includes a moveable member 537 positioned at least partially in the wall 52 defining the lumen 54 of the catheter 20 and a handle 538 to control the position of the movable member 537. The member 537 may be used to control the flow through the catheter 20 by positioning the member 537 in different rotational positions. The member 537 is sized and shaped to fit across the lumen 54 and control fluid flow therethrough. The member 537 may include a first opening 540 formed in the member 537 that allows flow through the catheter 20 at a first rate. The first opening 540 is shown in FIG. 16. The member 537 may include a second opening 542 formed in the member 537 allowing a second flow rate through the catheter 20. The second opening 542 is angularly offset from the first opening 540 by about 90°. The second opening 542 is larger than the first opening 540 such that the second flow rate is greater than the first flow rate.

Figure 17:
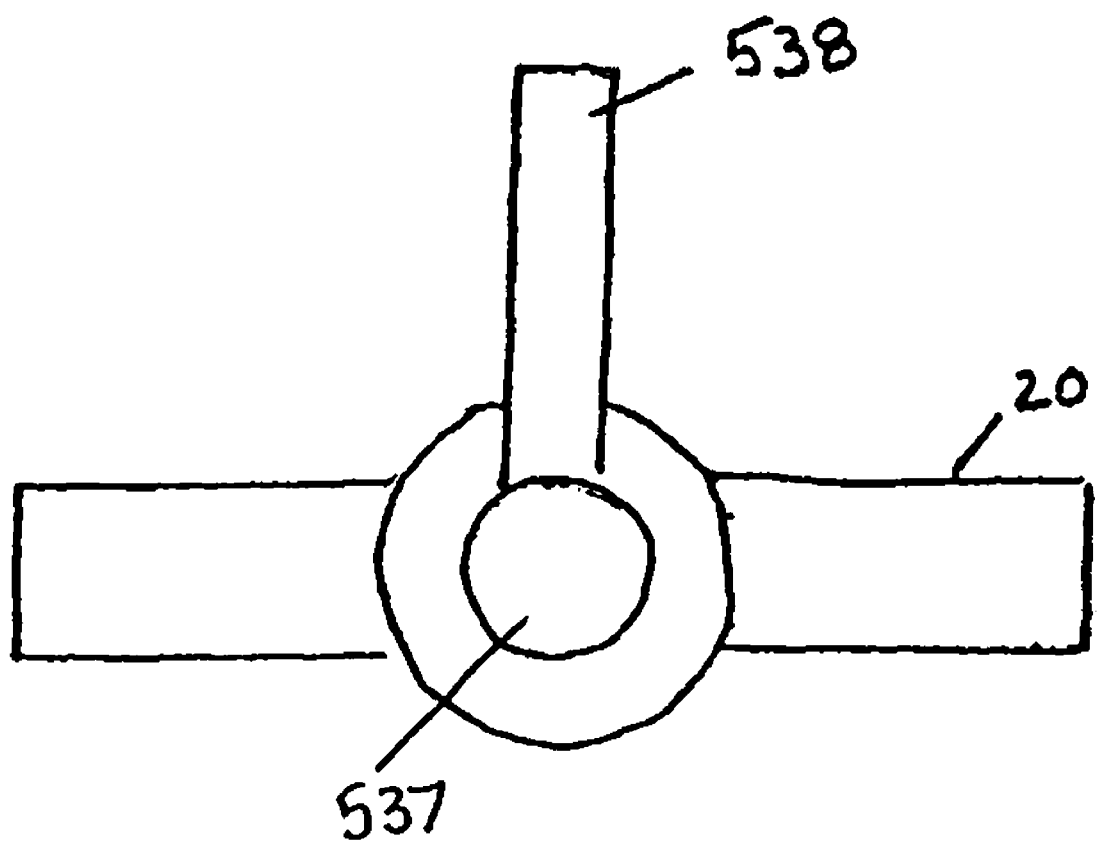
FIG. 17 is a top view of the embodiment shown in FIG. 13 showing the handle rotated.

The handle 538 is movable to rotate the member 537 to position the first opening 540 or the second opening 542 to be aligned with the lumen 54 of the catheter 20 to allow flow through the catheter 20. As shown in the side view in FIG. 16, when the handle 538 aligns with the catheter 20, fluid may flow through the second opening 542. When the handle 538 is rotated about 90° from the position as shown in FIG. 17, fluid may flow through the first opening 540. The handle 538 may be rotated about 45° from the position shown in FIG. 16 where neither the first opening 540 nor the second opening 542 is aligned with the lumen 54. This will prevent fluid from flowing through the lumen 54 of the catheter 20. Alternatively, a stopcock 28, described above, having open and closed positions to control flow into and out of the catheter 20, may be used in combination with the valve assembly 510.

In operation, the valve assembly 510 may be used to control flow in the first direction 532 from the opening of the catheter 20 to the balloon and in the second direction 534 from the balloon to the opening of the catheter 20. Preferably, the flow in the first direction 532 is at the first rate which is less than the flow in the second direction 534 at the second rate. For example, similar to the flow described above for the valve assembly 10, fluid may be introduced into the catheter using a syringe or by any method known to one of skill in the art. The member 537 may be aligned so that the handle 538 is about 90° rotated from alignment with the catheter 20, as shown in FIG. 17, and the opening 540 is aligned with the lumen 54 of the catheter 20 so that fluid flows in the first direction 532 through the first opening 540 at the first rate to inflate the balloon. To deflate the balloon, the handle 538 may be rotated to align the handle 538 with the catheter 20 to align the second opening 542 with the lumen 54 of the catheter 20 so that fluid may flow in the second direction at the second, higher rate.

In another embodiment of the present invention, shown in FIGS. 18-20B, a valve assembly 610 is illustrated. The valve assembly 610 includes a multiposition stopcock 612. The stopcock 612 may control the flow in a first direction 632 and a second direction 634 similar to the first and second directions 32, 34 described above where the flow in the first direction 632 flows from the medical device opening to the inflatable portion, for example, the balloon. The stopcock 612 includes a moveable member 637 and a handle 638 to control the position of the movable member 637. The movable member 637 may be positioned at least partially within the lumen of the catheter as described above to regulate the flow through the catheter in the first direction 632 and the second direction 634. The movable member 637 may include a groove 639, 649 that widens or deepens or both around a core 641 of the movable member 637.

For example, as shown in FIG. 18, when flow enters the valve assembly 610 at a first opening 650 in the first direction 632, the first flow rate through the valve assembly 610 and out a second opening 652 may be controlled by rotating the handle 638 to position the movable member 637. The movable member 637 may be rotated to different positions to control the rate of flow by changing the positioning of the groove 639 with respect to the first and second openings 650, 652. Rotating the handle 638 in a counter-clockwise direction will increase the flow rate in both the first and second directions as the area of the groove 639 increases. The position of the handle 638 with respect to the valve assembly 610 will determine the flow rate. As will be understood by one skilled in the art, a viewable portion of the valve assembly 610, for example a top portion, may include indicia correlating to the flow rate through the valve assembly 610 for 0-100% to assist the user in selecting the desired flow rate for the first direction 632 and the second direction 634. The movable member 637 may also include a solid portion 644 that closes the valve assembly 610 to prevent flow therethrough.

As shown in FIGS. 19A and 19B, alternative groove formations are possible. For example, in FIG. 19A, the groove 639 is shown as a continuous v-shaped groove that widens as the movable member 637 is rotated in the counter-clockwise direction to increase the flow rate. As shown in FIG. 19B, the groove 649 may include stepped gradations to control the flow rates as the movable member 637 is rotated in the counter-clockwise direction. One skilled in the art will understand that the valve assembly 610 may be configured to increase the flow rate through the valve assembly 610 when the movable member is rotated in the clockwise direction.

Figure 20A:
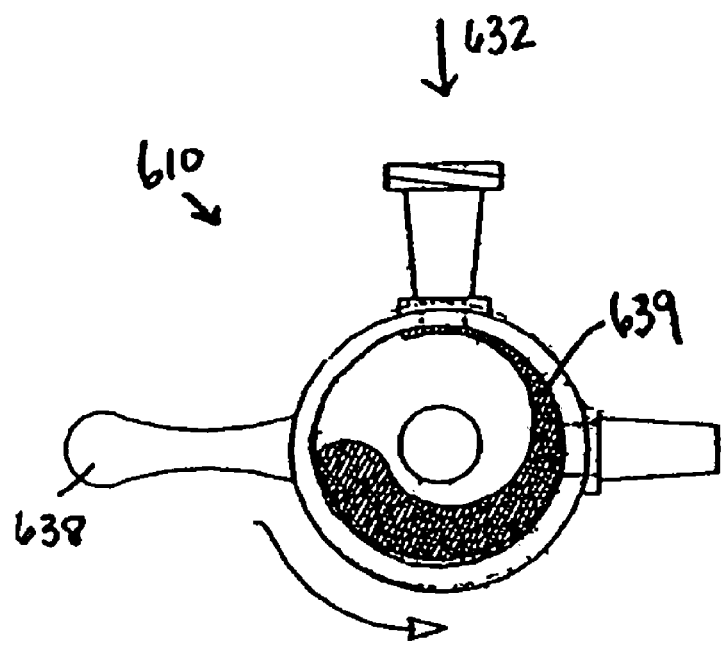
FIG. 20A is a side, sectional view of the embodiment shown in FIG. 18 with flow in a first direction.
Figure 20B:
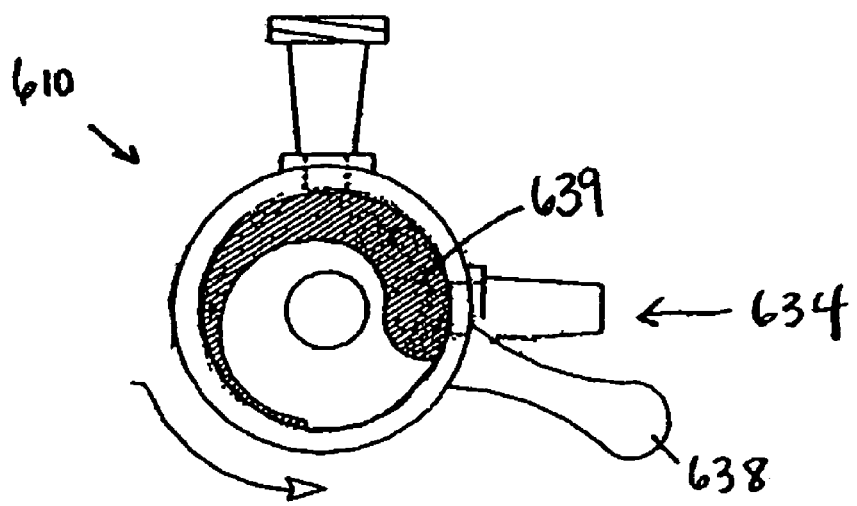
FIG. 20B is a side, sectional view of the embodiment shown in FIG. 18 with the handle rotated and flow in a second direction.

In operation, the valve assembly 610 may be used to control flow in the first direction 632 from the opening of the catheter to the balloon and in the second direction 634 from the balloon to the opening of the catheter. Preferably, the flow in the first direction 632 is at the first rate which is less than the flow in the second direction 634 at the second rate which is illustrated in FIGS. 20A and 20B, respectively. In the first direction 632, shown in FIG. 20A, the area of the groove 639 available though the openings 650, 652 is small, allowing for a lower flow rate in comparison to the position of the groove 639 shown in FIG. 20B. As shown in FIG. 20B, illustrating flow in the second direction 634, the handle 638 has been rotated in the counter-clockwise direction and thus, the area of the groove 639 available to through the openings 650, 652 is greater than the area of the groove 639 available through the openings 650, 652 shown in FIG. 20A, thereby allowing for a greater flow rate in the second direction 634. One skilled in the art will understand that a greater flow rate in the first direction 632 is possible, for example when the position of the handle 638 shown in FIG. 20B is used for flow in the first direction 632 and the position of the handle 638 shown in FIG. 20A is used for flow in the second direction 634.

It is therefore intended that the foregoing detailed description be regarded as illustrative rather than limiting, and that it be understood that it is the following claims, including all equivalents, that are intended to define the spirit and scope of this invention. It should be understood that a wide range of changes and modifications could be made to the preferred embodiments described above. In particular, some of the specific measurements noted herein may be changed without departing from the invention.

The invention claimed is:

1. A non-implantable valve assembly for controlling flow rates in a medical device, the valve assembly comprising:
   a valve member positioned at least partially within a wall defining an inflation lumen of the medical device, the inflation lumen connected to an inflatable member, the valve member comprising:
   a flow regulator comprising at least one flexible member controlling flow through the inflation lumen to the inflatable member for inflation and deflation of the inflatable member, the flexible member having a closed configuration for controlling a first inflation flow rate in a first direction and an open configuration for controlling a second deflation flow rate in a second direction; the flow regulator comprising a first opening defined in the flow regulator for allowing flow therethrough in the first direction and a second opening defined in the flow regulator and spaced apart from the first opening, the second opening allowing flow therethrough in the second direction; wherein the second rate is greater than the first rate.

2. The valve assembly of claim 1 wherein the valve member comprises an annular ring.

3. The valve assembly of claim 2 wherein the annular ring further comprises at least one opening defined in the annular ring for allowing flow therethrough in the second direction.

4. The valve assembly of claim 1 wherein the flow regulator comprises a pair of leaflets.

5. The valve assembly of claim 1 wherein the flow regulator comprises an annular flange extending radially outward.

6. The valve assembly of claim 5 further comprising a stem extending axially from the flange.

7. The valve assembly of claim 1 wherein the valve assembly is formed from an elastomer.

8. The valve assembly of claim 1 wherein the flow regulator comprises a multipositional member.

9. The valve assembly of claim 8 wherein the valve assembly further comprises a handle external to the medical device wherein the handle controls the position of the multipositional member to control the flow rates.

10. The valve assembly of claim 1 wherein the flow regulator is slidably positionable in the medical device.

11. A method of controlling flow in a medical device in a first direction and a second direction; the method comprising:
    providing a non-implantable valve assembly, the valve assembly comprising:
    a valve member being sized and shaped for reception at least partially within a wall defining an inflation lumen of the medical device, the inflation lumen connected to an inflatable member, the valve member comprising:
    a flow regulator for controlling flow rates in the first direction having a first rate and the second direction having a second rate, wherein the second rate is greater than the first rate;
    providing a plurality of first openings in the flow regulator for controlling flow in the first direction;
    providing a second opening in the valve member for controlling flow in the second direction, the second opening spaced apart from the plurality of first openings; and
    positioning the valve assembly in the inflation lumen of the medical device so that the flow regulator is movable between an open configuration for deflating the inflatable member in the second direction and a closed configuration for inflating the inflatable member in the first direction.

12. The valve assembly of claim 1, wherein the flow regulator comprises a plurality of first openings.

13. The valve assembly of claim 12, wherein the plurality of first openings are defined through the at least one flexible member.

14. The valve assembly of claim 1, wherein the assembly further comprises a flow actuator having an open position and a closed position for controlling flow therethough.

15. The valve assembly of claim 14, wherein the flow actuator is proximal to the flow regulator so that fluid flows past the flow actuator in the open position into the inflation lumen and through the flow regulator for inflation of the inflatable member.

16. The valve assembly of claim 4, wherein the valve assembly comprises a first end and a second end and wherein the pair of leaflets converge at the second end of the valve assembly to form a closure for the second opening in the closed configuration.

* * * * *